United States Patent [19]

Beasley et al.

[11] Patent Number: 6,159,963

[45] Date of Patent: *Dec. 12, 2000

[54] METHOD FOR TREATING SUBSTANCE ABUSE

[75] Inventors: Charles M Beasley, Indianapolis; Kurt Rasmussen, Fishers; Gary D Tollefson, Indianapolis, all of Ind.

[73] Assignee: Eli Lilly and Company, Indianapolis, Ind.

[ * ] Notice: This patent is subject to a terminal disclaimer.

[21] Appl. No.: 08/952,845

[22] PCT Filed: Mar. 10, 1997

[86] PCT No.: PCT/US97/03404

§ 371 Date: Nov. 25, 1997

§ 102(e) Date: Nov. 25, 1997

[87] PCT Pub. No.: WO97/33586

PCT Pub. Date: Sep. 18, 1997

[30] Foreign Application Priority Data

Mar. 29, 1996 [GB] United Kingdom .................... 9606615
Mar. 29, 1996 [GB] United Kingdom .................... 9606617

[51] Int. Cl.[7] .................................................... A61K 31/55
[52] U.S. Cl. .......................... 514/220; 514/810; 514/811; 514/813; 514/812

[58] Field of Search ...................................... 514/220, 810, 514/811, 812, 813

[56] References Cited

U.S. PATENT DOCUMENTS

| | | | |
|---|---|---|---|
| 5,229,382 | 7/1993 | Chakrabarti et al. .................... | 514/220 |
| 5,605,897 | 2/1997 | Beasley, Jr. et al. ..................... | 514/220 |
| 5,605,911 | 2/1997 | Olney et al. ............................. | 514/315 |
| 5,696,115 | 12/1997 | Rasmussen .............................. | 514/220 |

FOREIGN PATENT DOCUMENTS 0738 515  10/1996  European Pat. Off. .

OTHER PUBLICATIONS

Carlton K. Erickson, Alcohol & Alcoholism, 31 Suppl. 1:5–11, Mar. 1996.
Minzhang, et al., World Health Forum, 16(I): 1–9, discussion Oct. 27, 1995.

*Primary Examiner*—Kevin E. Weddington
*Attorney, Agent, or Firm*—Arleen Palmberg; Macharri Vorndran-Jones; Nancy J Harrison

[57] ABSTRACT

The invention provides a method for treating substance abuse comprising administering an effective amount of olanzapine or pharmaceutically acceptable salt thereof to a patient in need thereof.

38 Claims, No Drawings

METHOD FOR TREATING SUBSTANCE ABUSE

This invention provides a method for using 2-methyl-4-(4-methyl-1-piperazinyl)-10H-thieno[2,3-b][1,5]benzodiazepine, (hereinafter referred as "olanzapine"), for the treatment of dependence on a controlled substance. The present method provides a method for helping the patient to want to stop taking the drug, lessen the adverse symptoms of withdrawal from the drug and to minimize the relapse into abuse of the drug.

As long as history has been recorded, every society has used drugs that alter mood, thought, and feeling. In addition, pharmacological advances sometimes have been paralleled by physical as well as unfortunate behavioral dependence on agents initially consumed for therapeutic purposes. Therefore, the alleviation and eventual withdrawal from undesired physical and psychological dependence and tolerance of a substance has been a challenge throughout history. Although there are some treatments available for such withdrawal from addictive and/or mind altering substances, there is a great need for safer and more effective treatments.

It would be particularly desired to provide an effective treatment that could minimize hospitalization or institutionalization of a patient. The treatment must be non-addictive and provide a favorable side effect profile. It is particularly desired to provide a method that can help the patient want to stop taking the substance and ease the withdrawal effects when the patient stops taking the undesired substance. It is especially desired if the method minimizes the instances of relapse into abuse of the substance. Applicants believe that olanzapine could fulfill these needs.

It is known that olanzapine can provide antipsychotic activity. Olanzapine is a known compound and described in U.S. Pat. No. 5,229,382 as being useful for the treatment of schizophrenia, schizophreniform disorder, acute mania, mild anxiety states, and psychosis. U.S. Pat. No. 5,229,382 is herein incorporated by reference in its entirety. Surprisingly, and in accordance with this invention, Applicants have discovered that olanzapine can be useful for the treatment of substance abuse and withdrawal from such undesired physically and/or psychologically addictive substances.

The presently claimed invention provides a method for treating a condition which is a response produced by cessation and withdrawal from the abuse of a substance which is physically and/or psychologically addictive, comprising administering an effective amount of olanzapine or a pharmaceutically acceptable salt thereof to a patient in need of such treatment.

This invention further provides a method for treating substance abuse comprising administering an effective amount of olanzapine or a pharmaceutically acceptable salt thereof to a patient in need of such treatment.

This invention provides a method for treating dependence on a mind, thought or mood altering substance comprising administering an effective amount of olanzapine or a pharmaceutically acceptable salt thereof to a patient in need of or desiring such treatment.

This invention provides a method for assisting the patient to want to stop taking the mind, thought or mood altering substance. Further, this invention provides a method for easing the adverse withdrawal effects when the patient stops taking the undesired substance. Finally, this invention provides a method to minimize the instances of relapse into abuse of the substance.

Said substances include, but are in no way limited to opioids, anxiolytic and hypnotic drugs, cocaine, psychedelic agents, marijuana, amphetamines, hallucinogens, phencyclidine, and benzodiazepines. Said substances further include alcohol.

Finally, the present invention provides a method for treating alcohol withdrawal syndrome comprising administering an effective amount of olanzapine or a pharmaceutically acceptable salt thereof to a patient in need of such treatment.

Olanzapine is of the formula

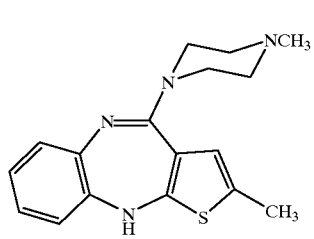

(I)

or an acid addition salt thereof.

It is especially preferred that olanzapine will be the Form II olanzapine polymorph having a typical x-ray powder diffraction pattern as represented by the following interplanar spacings:

| d |
|---|
| 10.2689 |
| 8.577 |
| 7.4721 |
| 7.125 |
| 6.1459 |
| 6.071 |
| 5.4849 |
| 5.2181 |
| 5.1251 |
| 4.9874 |
| 4.7665 |
| 4.7158 |
| 4.4787 |
| 4.3307 |
| 4.2294 |
| 4.141 |
| 3.9873 |
| 3.7206 |
| 3.5645 |
| 3.5366 |
| 3.3828 |
| 3.2516 |
| 3.134 |
| 3.0848 |
| 3.0638 |
| 3.0111 |
| 2.8739 |
| 2.8102 |
| 2.7217 |
| 2.6432 |
| 2.6007 |

A typical example of an x-ray diffraction pattern for Form II is as follows wherein d represents the interplanar spacing and $I/I_1$ represents the typical relative intensities:

| d | $I/I_1$ |
|---|---|
| 10.2689 | 100.00 |
| 8.577 | 7.96 |

-continued

| d | I/I$_1$ |
|---|---|
| 7.4721 | 1.41 |
| 7.125 | 6.50 |
| 6.1459 | 3.12 |
| 6.071 | 5.12 |
| 5.4849 | 0.52 |
| 5.2181 | 6.86 |
| 5.1251 | 2.47 |
| 4.9874 | 7.41 |
| 4.7665 | 4.03 |
| 4.7158 | 6.80 |
| 4.4787 | 14.72 |
| 4.3307 | 1.48 |
| 4.2294 | 23.19 |
| 4.141 | 11.28 |
| 3.9873 | 9.01 |
| 3.7206 | 14.04 |
| 3.5645 | 2.27 |
| 3.5366 | 4.85 |
| 3.3828 | 3.47 |
| 3.2516 | 1.25 |
| 3.134 | 0.81 |
| 3.0848 | 0.45 |
| 3.0638 | 1.34 |
| 3.0111 | 3.51 |
| 2.8739 | 0.79 |
| 2.8102 | 1.47 |
| 2.7217 | 0.20 |
| 2.6432 | 1.26 |
| 2.6007 | 0.77 |

The x-ray diffraction patterns set out herein were obtained using a Siemens D5000 x-ray powder diffractometer having a copper K$_a$ radiation source of wavelength, l=1·541 Å.

It is further preferred that the Form II olanzapine polymorph will be administered as the substantially pure Form II olanzapine polymorph.

As used herein "substantially pure" refers to Form II associated with less than about 5% Form I, preferably less than about 2% Form I, and more preferably less than about 1% Form I. Further, "substantially pure" Form II will contain less than about 0.5% related substances, wherein "related substances" refers to undesired chemical impurities or residual solvent or water. In particular, "substantially pure" Form II should contain less than about 0.05% content of acetonitrile, more preferably, less than about 0.005% content of acetonitrile. Additionally, it is preferred that the Form II should contain less than 0.5% of associated water.

The polymorph obtainable by the process taught in the '382 patent will be designated as Form I and has a typical x-ray powder diffraction pattern substantially as follows, obtained using a Siemens D5000 x-ray powder diffractometer, wherein d represents the interplanar spacing:

| d |
|---|
| 9.9463 |
| 8.5579 |
| 8.2445 |
| 6.8862 |
| 6.3787 |
| 6.2439 |
| 5.5895 |
| 5.3055 |
| 4.9815 |
| 4.8333 |
| 4.7255 |
| 4.6286 |
| 4.533 |

-continued

| d |
|---|
| 4.4624 |
| 4.2915 |
| 4.2346 |
| 4.0855 |
| 3.8254 |
| 3.7489 |
| 3.6983 |
| 3.5817 |
| 3.5064 |
| 3.3392 |
| 3.2806 |
| 3.2138 |
| 3.1118 |
| 3.0507 |
| 2.948 |
| 2.8172 |
| 2.7589 |
| 2.6597 |
| 2.6336 |
| 2.5956 |

A typical example of an x-ray diffraction pattern for Form I is as follows wherein d represents the interplanar spacing and I/I$_1$ represents the typical relative intensities:

| d | I/I$_1$ |
|---|---|
| 9.9463 | 100.00 |
| 8.5579 | 15.18 |
| 8.2445 | 1.96 |
| 6.8862 | 14.73 |
| 6.3787 | 4.25 |
| 6.2439 | 5.21 |
| 5.5895 | 1.10 |
| 5.3055 | 0.95 |
| 4.9815 | 6.14 |
| 4.8333 | 68.37 |
| 4.7255 | 21.88 |
| 4.6286 | 3.82 |
| 4.533 | 17.83 |
| 4.4624 | 5.02 |
| 4.2915 | 9.19 |
| 4.2346 | 18.88 |
| 4.0855 | 17.29 |
| 3.8254 | 6.49 |
| 3.7489 | 10.64 |
| 3.6983 | 14.65 |
| 3.5817 | 3.04 |
| 3.5064 | 9.23 |
| 3.3392 | 4.67 |
| 3.2806 | 1.96 |
| 3.2138 | 2.52 |
| 3.1118 | 4.81 |
| 3.0507 | 1.96 |
| 2.948 | 2.40 |
| 2.8172 | 2.89 |
| 2.7589 | 2.27 |
| 2.6597 | 1.86 |
| 2.6336 | 1.10 |
| 2.5956 | 1.73 |

The x-ray powder diffraction patterns herein were obtained with a copper K$_a$ of wavelength l=1.541 Å. The interplanar spacings in the column marked "d" are in Angstroms. The typical relative intensities are in the column marked "I/I$_1$".

As used herein the term "substance abuse" shall refer to the undesired physical and/or psychological dependence on a drug. It is most preferred that the term shall refer to dependence on a substance selected from the group consisting of opioids, anxiolytic and hypnotic drugs, cocaine, psychedelic agents, marijuana, amphetamines, hallucinogens, phencyclidine, and benzodiazepines. Additional compounds producing a physical and/or psychological dependence are contemplated as well. It is further preferred that the term shall refer to dependence on alcohol. It is an additional preferred embodiment that the term shall refer to dependence on nicotine.

As used herein the term "helping a patient to want to stop abusing" means that the thought altering effect of the physically or psychologically addictive substance is minimized to allow the patient to provide more rational thinking. Such rational thinking can be measured using standard scales or tools which are known to the artisan.

The term "mind, thought or mood altering substance" or "physically or psychologically addictive" shall refer to a substance which alters the thought process. For purposes of this invention, such substance additionally produces an undesired physical and/or psychological dependence or tolerance. Said substances shall include, but are in no way limited to a compound selected from the group consisting of opioids, anxiolytic and hypnotic drugs, cocaine, psychedelic agents, marijuana, amphetamines, hallucinogens, phencyclidine, and benzodiazepines. Such substances may include alcohol. Additionally, such substances may include nicotine.

The term "adverse withdrawal effects" shall refer to an adverse condition resulting from the cessation or withdrawal from substance abuse or withdrawal from a mind, mood or thought altering substance, wherein the adverse withdrawal effects are not otherwise attributable to another condition.

As used herein, the term "mammal" shall refer to the Mammalia class of higher vertebrates. The term "mammal" includes, but is not limited to, a human. The term "treating" as used herein includes prophylaxis in a patient susceptible to the named condition or amelioration or elimination of the condition once it has been established.

As used herein, the term "substance abuse" shall refer to a condition wherein the patient suffers physical consequences attributable to the ingestion of a substance and is unable or unwilling to cease such substance consumption and treatment to facilitate withdrawal from said substance is desired.

As used herein, the term "alcohol abuse" shall refer to a condition wherein the patient suffers physical consequences attributable to the ingestion of alcohol and is unable or unwilling to cease such alcohol consumption and treatment to facilitate withdrawal from alcohol consumption is desired.

As used herein, the term "alcoholism" or "physical dependence on alcohol" shall refer to a condition resulting from excessive consumption of alcohol. The patient suffering from alcoholism is identified by severe dependence or addiction and a cumulative pattern of behaviors associated with drinking. Frequent intoxication is obvious and destructive; it interferes with the individual's ability to socialize and to work. Many alcoholics experience marriage failure, work absenteeism which may lead to being fired. Alcoholics may seek medical treatment for their drinking, they may suffer physical injury associated with their drinking, and they may be apprehended while driving intoxicated. Eventually, the alcoholic may be arrested for drunkedness and/or hospitalized for delirium tremens or cirrhosis of the liver.

As used herein, "alcohol withdrawal" shall refer to a characteristic withdrawal syndrome that develops after the cessation of (or reduction in) heavy and prolonged alcohol use. Alcohol withdrawal syndrome is summarized in *Goodman & Gillman's The Pharmacological Basis of Therapeutics,* 563 (9th Ed. 1996, McGraw-Hill, New York). To further clarify, Alcohol Withdrawal is characterized in the DSM-IV-R. *Diagnostic and Statistical Manual of Mental Disorders, Revised,* 3rd Ed. (1994) as catagory 291.8. The DSM-IV-R was prepared by the Task Force on Nomenclature and Statistics of the American Psychiatric Association, and provides clear descriptions of diagnostic catagories. The skilled artisan will recognize that there are alternative nomenclatures, nosologies, and classification systems for pathologic psychological conditions and that these systems evolve with medical scientific progress.

The discontinuation or a reduction of excessive alcohol consumption typically results in alcohol withdrawal syndrome. Alcohol withdrawal syndrome is a continuum of symptoms and signs which accompany alcohol withdrawal, usually beginning 12 to 48 hours after a significant decrease in alcohol intake. For example, such symptoms may include tremor, weakness, sweating, gastrointestinal symptoms, increasing confusion, poor sleep, and/or severe depression. These symptoms often cause clinically significant distress or impairment in social, occupational, or other important areas of functioning. The present invention is most preferably used to alleviate symptoms attributed to alcohol withdrawal when such symptoms are not due to a general medical condition and are not better accounted for by a mental disorder.

The present invention further alleviates negative symptoms of withdrawal from the mind, thought or mood altering substance wherein such symptoms are not due to a general medical condition and are not better accounted for by a mental disorder.

The method of the present invention is preferably administered in connection with an educational and/or behavioral modification program to ensure continued abstinence from alcohol. The method of the present invention is also highly beneficial to such programs by alleviating the suffering experienced from the alcohol withdrawal over the course of such programs. Therefore, the programs can be more effective by focusing on educational and behavioral modification goals, further reducing the incidence of program non-completion.

The results of pharmacological studies show that olanzapine has muscarinic cholinergic receptor activity. The compound is active at the dopamine D-1 and D-2 receptors as indicated by an IC50 of less than 1 uM in the 3H-SCH233390 (Billard, et al. Life Sciences 35:1885 (1984)) and the 3H spiperone (Seeman et al Nature 216:717 (1976)) binding assays respectively. Further, olanzapine is active at the 5-HT-2 receptor and 5-HT1C receptor. The complex pharmacological profile of the compound provides a medicament which can be useful for the treatment of a condition resulting from cessation and withdrawal from the use of a substance which the patient had developed a dependence on. Further, the complex pharmacological profile of the compound provides a medicament which can be useful to modulate the medial forebrain bundle to interfere with the 'pleasure pathway' mediated perpetuation of the abuse cycle. See C. K. Erickson, Alcohol & Alcoholism, 31 Sup. 1, pp 5–11 (1996).

The usefulness of the compound for treating a condition resulting from cessation and withdrawal from the use of a dependence producing substance can be supported by the following studies as described.

I. Auditory Startle Response.

Male Long Evans rats (Harlan Sprague Dawley) are individually housed in a controlled environment on a 12 hour light-dark cycle. The rats are given free access to food and water. All treatment groups contain from 8 to 10 rats.

The rats are anesthetized with halothane and Alzet osmotic minipumps (Alza Corporation, Palo Alto, Calif.) are implanted subcutaneously. A dependence producing substance, such as an opioid, is provided in physiological saline. Pumps are filled with opioid (6 mg/kg base/day) or the appropriate vehicle. Twelve days following implantation of pumps, rats are anesthetized with halothane and the pumps are removed. (The study is also conducted with other dependence producing substances such as marijuana, and so on.)

The auditory Startle Response is observed.

The sensory motor reactions [auditory startle response (peak amplitude, $V_{max}$)] of individual rats are recorded using San Diego Instruments startle chambers (San Diego, Calif.). Startle sessions consist of a 5 minute adaptation period at background noise level of 70+/−2 dBA immediately followed by 25 presentations of auditory stimuli (120+/−3 dBA noise, 50 ms duration) presented at 8 second intervals. Peak startle amplitudes are averaged for all 25 presentations of stimuli for each session. Auditory startle responding is evaluated daily at 24 hour intervals on days 1–4 following substance withdrawal.

Further, the usefulness of the compound for helping the patient to want to stop taking an undesired addictive substance, to lessent the adverse withdrawal symptoms, and to minimize the incidence of relapse into abuse can be shown using the following study:
Clinical observations.

A double-blind multicenter clinical trial was designed to assess the safety and efficacy of olanzapine. Patients were randomized to olanzapine or placebo. The results of the study suggest that olanzapine can be useful for the treatment of addictive substance withdrawal.

Olanzapine is effective over a wide dosage range, the actual dose administered being dependent on the condition being treated. For example, in the treatment of adult humans, dosages of from about 0.25 to 50 mg, preferably from 1 to 30 mg, and most preferably 1 to 25 mg per day may be used. A once a day dosage is normally sufficient, although divided doses may be administered. For treatment of a condition resulting from cessation and withdrawal from the use of an addictive substance, a dose range of from 1 to 30 mg, preferably 1 to 20 mg per day is suitable. For the treatment of alcohol abuse, a lower dosage may be more appropriate. Likewise, for the treatment of the cessation of nicotine consumption, a lower dosage may be more appropriate.

A preferred formulation of the invention is a solid oral formulation comprising from about 1 to about 25 mg or 1 to 15 mg of olanzapine as an effective amount of the active ingredient.

Most preferably, the solid oral formulation is contained in packaging materials which protect the formulation from moisture and light. For example, suitable packaging materials include amber colored high density polyethylene bottles, amber colored glass bottles, and other containers made of a material which inhibits the passage of light. Most preferably, the packaging will include a desiccant pack. The container may be sealed with an aluminum foil blister to provide the desired protection and maintain product stability.

Olanzapine will normally be administered orally or by injection and, for this purpose, it is usually employed in the form of a pharmaceutical composition.

Accordingly, pharmaceutical compositions comprising olanzapine, as active ingredient associated with a pharmaceutically acceptable carrier may be prepared. In making the compositions of the invention conventional techniques for the preparation of pharmaceutical compositions may be used. For example, the active ingredient will usually be mixed with a carrier, or diluted by a carrier, or enclosed within a carrier which may be in the form of a capsule, sachet, paper or other container. When the carrier serves as a diluent, it may be solid, semi-solid or liquid material which acts as a vehicle, excipient or medium for the active ingredient. The active ingredient can be adsorbed on a granular solid container for example in a sachet. Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxy-benzoate, talc, magnesium stearate or mineral oil. The compositions of the invention may, if desired, be formulated so as to provide quick, sustained or delayed release of the active ingredient after administration to the patient.

Depending on the method of administration, the compositions for the treatment of central nervous system conditions may be formulated as tablets, capsules, injection solutions for parenteral use, gel or suspension for transdermal delivery, suspensions or elixirs for oral use or suppositories. Preferably the compositions are formulated in a unit dosage form, each dosage containing from 0.25 to 25 mg, more usually 1 to 25 mg, of the active ingredient.

The materials for the present invention can be purchased or prepared by a variety of procedures well known to those of ordinary skill in the art. Olanzapine can be prepared as described by Chakrabarti in U.S. Pat. No. 5,229,382 ('382), herein incorporated by reference in its entirety. Further, the following preparations illustrate a method for preparing of the especially preferred Form II olanzapine polymorph.

Compound characterization methods include, for example, x-ray powder pattern analysis, thermogravimetric analysis (TGA), differential scanning calorimetery (DSC), titrametric analysis for water, and $H^1$-NMR analysis for solvent content.

The following examples are provided for purposes of illustration and are not to be construed as limiting the scope of the claimed invention.

PREPARATION 1

Technical Grade Olanzapine

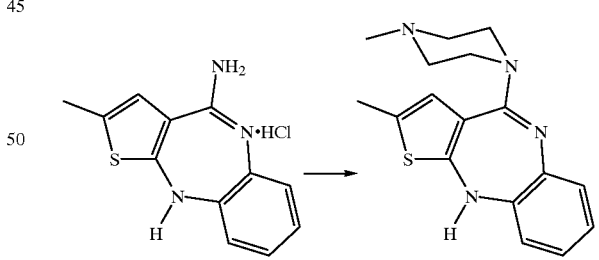

Intermediate 1
In a suitable three neck flask the following was added:
Dimethylsulfoxide (analytical): 6 volumes
Intermediate 1: 75 g
N-Methylpiperazine (reagent): 6 equivalents
Intermediate 1 can be prepared using methods known to the skilled artisan. For example, the preparation of the Intermediate 1 is taught in the '382 patent.

A sub-surface nitrogen sparge line was added to remove the ammonia formed during the reaction. The reaction was heated to 120° C. and maintained at that temperature throughout the duration of the reaction. The reactions were followed by HPLC until ≲5% of the intermediate 1 was left unreacted. After the reaction was complete, the mixture was allowed to cool slowly to 20° C. (about 2 hours). The reaction mixture was then transferred to an appropriate three neck round bottom flask and water bath. To this solution with agitation was added 10 volumes reagent grade methanol and the reaction was stirred at 20° C. for 30 minutes. Three volumes of water was added slowly over about 30 minutes. The reaction slurry was cooled to zero to 5° C. and stirred for 30 minutes. The product was filtered and the wet cake was washed with chilled methanol. The wet cake was dried in vacuo at 45° C. overnight. The product was identified as technical olanzapine.

Yield: 76.7%; Potency: 98.1%

PREPARATION 2

Form II Olanzapine Polymorph

A 270 g sample of technical grade 2-methyl-4-(4-methyl-1-piperazinyl)-10H-thieno[2,3-b][1,5]benzodiazepine was suspended in anhydrous ethyl acetate (2.7 L). The mixture was heated to 76° C. and maintained at 76° C. for 30 minutes. The mixture was allowed to cool to 25° C. The resulting product was isolated using vacuum filtration. The product was identified as Form II using x-ray powder analysis.

Yield: 197 g.

The process described above for preparing Form II provides a pharmaceutically elegant product having potency ≧97%, total related substances <0.5% and an isolated yield of >73%.

EXAMPLE 1

A portion of the hydroxypropyl cellulose was dissolved in purified water to form a solution for granulation. The remaining hydroxypropyl cellulose (total of 4.0% w/w final tablet weight), which was an extra fine grade, was combined with the olanzapine (1.18% w/w), lactose (79.32% w/w) and a portion of the crospovidone (5% w/w) in a high shear granulator. All ingredients were security sieved prior to addition and dry blended in the granulator. This mixture was then granulated with the hydroxypropyl cellulose solution in the high shear granulator. The granulation was wet sized using standard methods. The wet granulation was then dried in a fluidized bed dryer and sized. The material was then added to a tumble bin mixer.

The running powders consisting of microcrystalline cellulose (granular) (10% w/w), magnesium stearate (0.5% w/w), and the remainder of the crospovidone were added to the sized granulation. The mixture was blended and compressed with the appropriate tooling on tablet compression equipment.

Subcoating:

Hydroxypropyl methylcellulose (10% w/w) was mixed with purified water to form a solution. Core tablets were divided into approximately equal sections and spray coated with the hydroxypropyl methylcellulose solution. The operation was performed in a perforated coating pan.

Coating of Core Tablets:

Color Mixture White (hydroxypropyl methylcellulose, polyethylene glycol, polysorbate 80, and titanium dioxide) was mixed with purified water to form the coating suspension. Subcoated tablets were divided into approximately equal sections and spray coated with the coating suspension described above. The operation was performed in a perforated coating pan.

The coated tablets were lightly dusted with carnauba wax and imprinted with appropriate identification.

What is claimed is:

1. A method for treating substance abuse in a mammal comprising administering an effective amount of olanzapine, or a pharmaceutically acceptable salt thereof, to the mammal.

2. A method of claim 1 wherein the substance abuse is physical dependence on a compound selected from the group consisting of opioids, anxiolytic and hypnotic drugs, cocaine, psychedelic agents, marijuana, amphetamines, hallucinogens, phencyclidine, and benzodiazepines.

3. A method of claim 2 wherein the compound is selected from the group consisting of anxiolytic and hypnotic drugs, cocaine, psychedelic agents, amphetamines, hallucinogens, phencyclidine, and benzodiazepines.

4. A method of claim 2 wherein the compound is an opioid.

5. A method of claim 1 wherein the olanzapine is Form II olanzapine polymorph.

6. A method of claim 2 wherein the olanzapine is Form II olanzapine polymorph.

7. A method for treating a patient suffering from a condition which is a response produced by withdrawal from the use of a physically or psychologically addictive substance, comprising administering an effective amount of olanzapine, or a pharmaceutically acceptable salt thereof, to the patient.

8. A method of claim 7 wherein the response is substance withdrawal syndrome.

9. A method of claim 7 wherein the olanzapine is Form II olanzapine polymorph.

10. A method of claim 7 wherein the effective amount is from about 1 mg to about 25 mg per day.

11. A method of claim 9 wherein the effective amount is from about 1 mg to about 20 mg per day.

12. A method for helping a patient want to stop substance abuse wherein the substance is physically or psychologically addictive, comprising administering an effective amount of olanzapine, or a pharmaceutically acceptable salt thereof, to the patient.

13. A method of claim 12 wherein the substance is a compound selected from the group consisting of opioids, anxiolytic and hypnotic drugs, cocaine, psychedelic agents, marijuana, amphetamines, hallucinogens, phencyclidine, and benzodiazepines.

14. A method of claim 13 wherein the compound is selected from the group consisting of anxiolytic and hypnotic drugs, cocaine, psychedelic agents, amphetamines, hallucinogens, phencyclidine, and benzodiazepines.

15. A method of claim 13 wherein the compound is an opioid.

16. A method of claim 15 wherein the olanzapine is Form II olanzapine polymorph.

17. A method for helping a patient to want to stop abusing a mind, thought or mood altering substance comprising administering an effective amount of olanzapine or a pharmaceutically acceptable salt thereof to the patient.

18. A method of claim 17 wherein the substance is alcohol.

19. A method of claim 16 wherein the substance is a compound selected from the group consisting of opioids, anxiolytic and hypnotic drugs, cocaine, psychedelic agents, marijuana, amphetamines, hallucinogens, phencyclidine, and benzodiazepines.

20. A method of claim 19 wherein the compound is cocaine, an opioid or an amphetamine.

21. A method for easing the adverse effects in a mammal of withdrawing from a mind, thought or mood altering substance which is physically or psychologically addictive, comprising administering an effective amount of olanzapine or a pharmaceutically acceptable salt thereof to the mammal.

22. A method of claim 21 wherein the substance is alcohol.

23. A method of claim 21 wherein the substance is a compound selected from the group consisting of opioids, anxiolytic and hypnotic drugs, cocaine, psychedelic agents, marijuana, amphetamines, hallucinogens, phencyclidine, and benzodiazepines.

24. A method of claim 23 wherein the compound is cocaine, an opioid or an amphetamine.

25. In a mammal physically addicted to a mind, thought or mood altering substance, a method for minimizing the frequency of relapse to abuse of the substance, comprising administering an effective amount of olanzapine, or a pharmaceutically acceptable salt thereof, to the mammal.

26. A method of claim 25 wherein the substance is a compound selected from the group consisting of opioids, anxiolytic and hypnotic drugs, cocaine, psychedelic agents, marijuana, amphetamines, hallucinogens, phencyclidine, and benzodiazepines.

27. A method of claim 25 wherein the substance is alcohol.

28. A method of claim 25 wherein the mammal had become physically addicted to the substance within the previous two years.

29. A method for treating alcohol abuse in a mammal comprising administering an effective amount olanzapine, or a pharmaceutically acceptable salt thereof, to the mammal.

30. A method of claim 29 wherein the olanzapine is Form II olanzapine polymorph.

31. A method of claim 29 wherein the alcohol abuse is physical dependence on alcohol.

32. A method of claim 28 wherein the olanzapine is Form II olanzapine polymorph.

33. A method of claim 32 wherein the physcial dependence on alcohol is alcoholism.

34. A method for treating a patient suffering from a condition produced by withdrawal from the abuse of alcohol, comprising administering an effective amount of olanzapine, or a pharmaceutically acceptable salt thereof, to the patient.

35. A method of claim 34 wherein the condition is alcohol withdrawal syndrome.

36. A method of claim 34 wherein the effective amount is from about 1 mg to about 25 mg per day.

37. A method of claim 34 wherein the olanzapine is Form II olanzapine polymorph.

38. A method of claim 37 wherein the effective amount is from about 1 mg to about 20 mg per day.

* * * * *